United States Patent [19]
Dittmann et al.

[11] Patent Number: 5,908,552
[45] Date of Patent: Jun. 1, 1999

[54] COLUMN FOR CAPILLARY CHROMATOGRAPHIC SEPARATIONS

[75] Inventors: Monika Dittmann, Marxzell; Gerard Rozing; Hans-Peter Zimmermann, both of Karlsruhe, all of Germany

[73] Assignee: Hewlett-Packard Company, Palo Alto, Calif.

[21] Appl. No.: 08/948,878

[22] Filed: Oct. 10, 1997

Related U.S. Application Data

[63] Continuation of application No. 08/761,046, Dec. 5, 1996, abandoned.

[30] Foreign Application Priority Data

Dec. 14, 1995 [EP] European Pat. Off. .............. 95119699

[51] Int. Cl.$^6$ ................................. B01D 15/08
[52] U.S. Cl. ..................... 210/198.2; 210/656; 96/101; 204/601
[58] Field of Search .................................. 204/601, 603, 204/604, 605; 210/635, 656, 198.2; 96/101

[56] References Cited

U.S. PATENT DOCUMENTS

| 3,782,078 | 1/1974 | Jerpe ................................... | 210/198.2 |
| 4,293,415 | 10/1981 | Bente .................................. | 210/198.2 |
| 4,793,920 | 12/1988 | Cortes .................................. | 210/198.2 |
| 5,061,361 | 10/1991 | Gordon ................................. | 204/603 |
| 5,246,577 | 9/1993 | Fuchs et al. ......................... | 210/198.2 |

FOREIGN PATENT DOCUMENTS

0328146A2  8/1989  European Pat. Off. ............ 210/198.2

OTHER PUBLICATIONS

European Search Report, Jun. 26, 1996, EP 95 11 9699, pp. 1–4.

Analytical Methods and Instruments, vol. 2, No. 3, pp. 122–128, Hong Chen et al., "On–Column UV Absorption Detection in Liquid Chromatography with Packed Capillaries", 1995.

Chromatographia, vol. 40, No. 5/6, Mar. 1995, pp. 329–335, R. J. Boughtflower et al., "Capillary Electrochromatography–Some Important Considerations in the Preparation of Packed Capillaries and the Choice of Mobile Phase Buffers".

*Primary Examiner*—Ernest G. Therkorn

[57] ABSTRACT

A column for capillary chromatographic separations, for example high performance liquid chromatography, capillary electrochromatography, or supercritical chromatography, includes a column bed of packing material arranged in the inner bore of the column, and a retainer for retaining the column bed in the interior of the column, wherein the retainer includes regions in the interior of the column having radial dimensions which are different from that of the inner bore. Preferably, the column is a fused silica capillary whose protective layer is removed in a detection area so that sample substances separated in the column can be detected by means of a light source which transmits radiation through the column which is detected by a detector.

9 Claims, 1 Drawing Sheet

COLUMN FOR CAPILLARY CHROMATOGRAPHIC SEPARATIONS

This is a continuation of application Ser. No. 08/761,046 filed on Dec. 05, 1996, now abandoned.

FIELD OF THE INVENTION

The invention relates to a column for capillary chromatographic separations, for example for high performance liquid chromatography, or capillary electrochromatography, or supercritical chromatography.

BACKGROUND OF THE INVENTION

Capillary chromatographic separation methods are preferably performed in fused silica (FS) tubing with internal diameters ranging from 5–530 µm. Such tubing consists of a silica ($SiO_2$) glass drawn at high temperature (1300° C.) from a quartz preform provided with a protective outside layer from polyimide or aluminum. Robustness, tensile strength, high pressure resistance and bend stability are favorable mechanical properties of fused silica tubing. High chemical purity and well defined surface of the tubing provides in most cases low interaction with solutes and leads to optimum separation in many applications.

In U.S. Pat. No. 4,293,415 Dandeneau et al. describe the usage of a fused silica capillary, which may have wall coatings on the inside surface to stimulate specific interactions and/or further minimize secondary undesired solute/surface interactions, for open tubular capillary gas chromatography (CGC) and open tubular supercritical fluid chromatography (SFC). Jorgenson et al. have demonstrated that such capillaries are also ideally suited for the newer technique of capillary electrophoresis (CE).

It has been demonstrated that FS tubing can also be used for capillary separations performed in a packed bed, such as SFC, micro high performance liquid chromatography, and capillary electrochromatography (CEC). The mechanical properties of fused silica capillaries suffice to withstand the high pressure that occurs either when packing the tubing with small particles using a high pressure filtration technique or when operating the column especially in high performance liquid chromatography mode.

The main problem in packing fused silica or other tubing with small inner diameter is that the packing material in the column bed needs to be retained in the tubing; otherwise hydraulic or electrical forces drive the particles out of the capillary column. In a conventional high performance liquid chromatography column the packed bed is typically kept in place under the high pressure that is applied (up to 400 bar) by terminating plates or sieves, called frits, that are porous to the liquid but too narrow for the particles to move through. Because these frits need to be firmly attached to the packed bed, a fitting is needed which compresses the frit to the bed and at the same time resists the high pressure. In conventional high performance liquid chromatography columns, stainless steel fittings are used that are clamped to the column tube outside.

Due to the narrow outer diameter of the fused silica capillary tubing, typically 0.350 mm, and the small volumes involved in the separation, it is not very well possible to use external fittings even if they are reduced in size accordingly.

Several groups therefore have pursued the principal approach to immobilize part of the packed bed in the capillary by chemical means. E.g. Heman Cortez et al. in U.S. Pat. No. 4,793,920 describe the usage of KaSil (potassium silicate) to form a porous ceramic frit in the fused silica tube which will retain the small particles during column packing. Columns with frit terminators made in this way have internal diameters typically in the 180–530 µm range and have been used in SFC preferably.

In micro high performance liquid chromatography and the new field of capillary electrochromatography (CEC) narrower columns—interior diameter <200 µm—are used. In this field, several groups have pursued other approaches to form such a frit. In U.S. Pat. No. 5,246,577 Fuchs et al. bring fusable glass beads, 1–50 µm diameter into the fused silica capillary tube and melt these together under electrical sparking.

Unmodified silica particles 3–40 µm diameter have been used alternatively. After bringing these into the fused silica capillary tube, particles were glued together by destabilization of a tetraalkoxysilane forming in situ silicic acid binding the particles together.

In recent publications the stationary phase particles have been immobilized directly in the packed bed by application of heat to a zone of the packed fused silica column where the terminating frit needs to be while the column still is at high pressure on the packing apparatus (e.g. Boughtflower et al., Chromatographia 40, 329 (1995), Smith et al., Chromatographia 38, 649 (1994), Rozing et al., LC-GC Magazine, October 1995). It is believed that under these conditions the particles are glued together by the fact that upon heating a small amount of silica dissolves in water forming silicic acid, and that upon cooling the repolymerized silicic acid deposits between the particles. The advantage of this approach is that it does not substantially alter the chemical constitution of the zone that is fritted, that it can be done on the inlet and outlet side without problem, that the length of the fritted zone is well controlled by the dimension of the external heating source used and that the porosity of the bed is unaffected. Photographs e.g. by Boughtflower et al., show that the particle structure is not affected by this treatment and therefore interparticle porosity is maintained.

The main problem with all these approaches is to obtain chemical or physical adhesion of the fritted zone to the inner capillary wall so that the fritted zone has sufficient stability to overcome shrinking and cracking of the bed or fritted zone. It has been observed that after drying out of a packed capillary the frits loose contact to the inner capillary wall and gentle electrical or hydraulic force on the bed suffices to drive out the packing and destroy the column. With all approaches to generate internal frits in a packed capillary column attachment of the fritted zone to the inside wall of the capillary remains a potential problem.

SUMMARY OF THE INVENTION

It is thus an object of the present invention to provide a packed column for capillary chromatography wherein the packing material is retained in a simple and effective manner.

In particular, it is an object of the invention to avoid or reduce the above mentioned problems associated with known techniques for retaining the packing material in the column.

A column according to the invention for capillary chromatographic separations, for example high performance liquid chromatography, capillary electrochromatography, or supercritical chromatography, comprises a column bed of packing material arranged in the inner bore of the column and means for retaining the column bed in the interior of the column, wherein the means for retaining the column bed comprise a region in the interior of the column the radial dimension of which is different from that of the inner bore. The radial dimension of said region can either be larger than the diameter of the inner bore (extension) or it can be smaller (constriction).

According to a preferred embodiment of the present invention, the mentioned prior art problems are circumvented in the following way. The fused silica tubing that is used for preparation of a micro high performance liquid chromatography or CEC column has at the positions where the fritted zones are projected a little elongation in radial direction, i.e. a bubble with an extension factor (ratio of bubble diameter to tube diameter) of approx. 1.5. With a fused silica tube prepared in this way, a packed column is prepared in the usual way (see e.g. Boughtflower et al., Rozing et al.). The zones containing the bubble are packed as well. After the column packing is finished, the fritted zone is generated in the way as described above. However, the fritted zone is of larger interior diameter than the empty tube preceding or following it. As a consequence, even if the fritted packing material starts to loose the chemical adhesion to the wall by cracking or shrinking, the plug of immobilized packing material is too wide to move through the fused silica tube, stays in place and will continue to retain the packing material.

In accordance with a further development of the invention, improved optical detection of sample substances separated in the column is possible. Ultraviolet/visible (UV-VIS) photometric detection in capillary high performance liquid chromatography and CEC is done by 'on-column' measurement of changes in transmittance of the incident light. To that end, a small stretch of the protective layer is removed to allow unhindered irradiation of the fused silica tube. Because the path of the light through the capillary is limited to its diameter, comparatively low extinction values for the eluting peaks are obtained and therefore capillary liquid phase separation techniques may hamper sensitivity of spectrophotometric absorbance detection. The sensitivity can be improved substantially by elongation of the tube diameter locally, i.e. by the formation of a bubble as in connection with the fritted zone. A detection bubble as such is described in U.S. Pat. No. 5,061,361.

Since the fused silica tube used for the manufacture of a capillary column for micro high performance liquid chromatography and CEC contains two bubbles to accept the fritted zone, a detection bubble with a ratio of bubble diameter to tube diameter >2 can be generated in the same manufacturing process. In a preferred embodiment, a column for CEC and micro high performance liquid chromatography has two bubbles to retain the fritted zone and a detection bubble.

According to a further embodiment of the invention, "in-column-detection" of sample substances is possible. "In-column-detection" has already been proposed for capillary separation techniques (see e.g C. s. Horvath et al., Analytical Methods and Instrumentation, 2(3), 122–128 (1995), E. J. Guthrie et al., Anal. Chem., 56, 483, (1984), but with a different type of column than the present invention. "In-column-detection" means that UV-VIS photometric detection is done on packed fused silica capillary columns through the packed bed. A certain translucency of the bed a the wavelength of detection is mandatory for this purpose. The rationale behind this idea is that peaks that are retained will be on the column bed in a shorter, longitudinal zone than after leaving the packed bed and therefore will be more concentrated. In accordance with an embodiment of the invention, detection takes place through the fritted zone thereby further enhancing detection by the longer pathlength.

Subsequently, preferred embodiments of the invention will be explained with reference to the drawings.

DETAILED DESCRIPTION OF THE PREFERRED EMBODIMENTS

Figure 1:
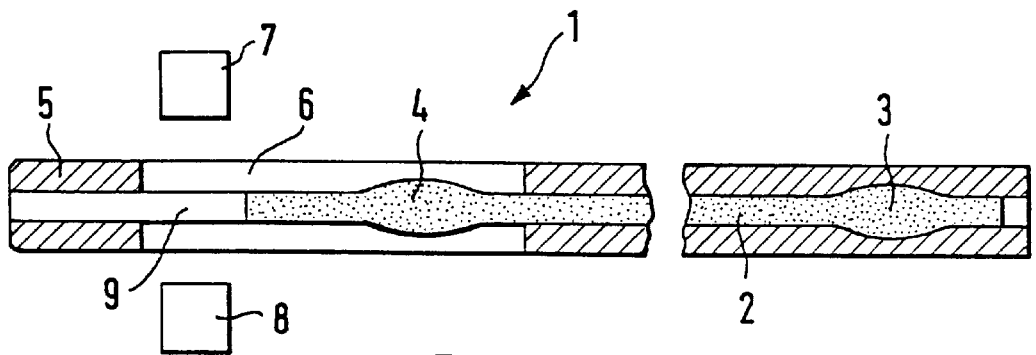
FIG. 1 is a schematic diagram of a first embodiment of the invention.

FIG. 1 shows a packed column 1 according to a-first embodiment of the invention. The column is made of fused silica and typically has a length of about 5–200 cm. FIG. 1 only shows the end portions of such a column. The column has an interior diameter in the range between about 5–530 micrometers. The interior of the column is filled over the major part of its length with a packed bed 2 which serves for separating the sample substances passing through the column. The two ends of the column 1 comprise zones 3 and 4 where the interior diameter is enlarged relative to the interior diameter of the rest of the column. These enlarged zones 3, 4 are also referred to as "bubbles". The bubbles 3 and 4 are filled with packing material (grey area) as is the area in the column between the two bubbles. The plug of packing material is too large to move to areas of smaller diameter inside the column. Consequently, the packing material is retained in the column by the plugs.

FIG. 1 also illustrates how sample detection with a column of the invention can be performed. The protective layer 5 of the column 1 is removed in a detection area 6 so that light from a light source 7, typically in the ultraviolet/visible spectral range, can pass through the column 1 and the sample in an area 9 of the column where there is no packing material. The light intensity which has been modified by the sample is detected by a detector 8. The signals provided by the detector can be used for qualitative and quantitative analysis of the sample.

Figure 2:
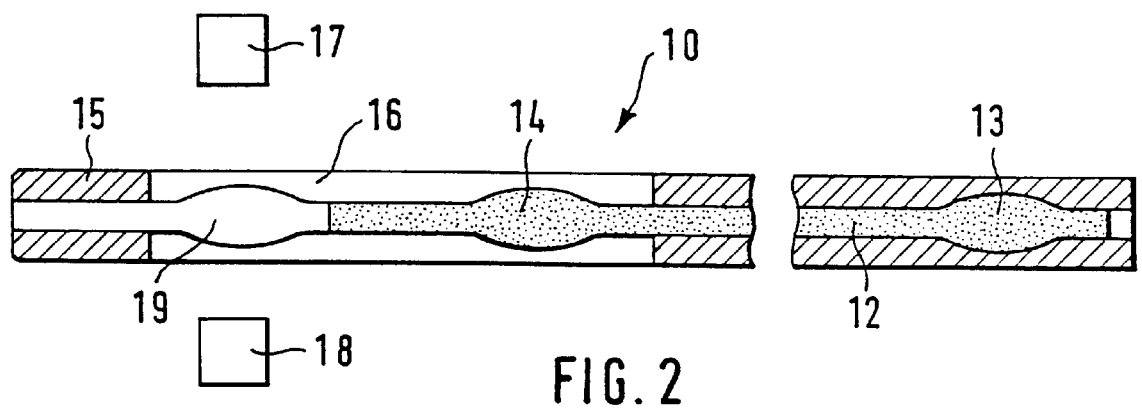
FIG. 2 is a schematic diagram of a second embodiment of the invention with an additional detection bubble.

FIG. 2 shows a second embodiment of the invention wherein the column 10 also comprises bubbles 13 and 14 which are filled with packing material 12. The protective layer 15 of the column is removed in an area 16. The difference to the embodiment of FIG. 1 is that the detection area where light from a light source 17 passes through the column comprises widened area ("bubble") 19 similar to the bubbles 13 and 14. The bubble 19 is free from packing material. Due to the greater interior diameter of the bubble 19 as compared to the rest of the column, the path length for the light passing through it is increased, thus leading to a substantially increased detection sensitivity. The light which has been modified by the sample in the bubble 19 is detected by a detector 18.

Figure 3:
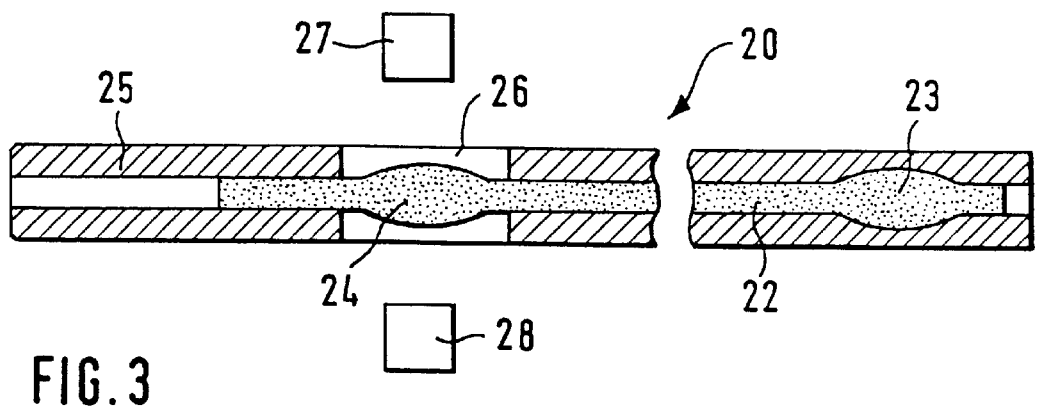
FIG. 3 schematically shows a third embodiment of the invention wherein detection bubble and retaining bubble coincide.

A third embodiment of the invention is shown in FIG. 3, wherein the packing material 22 in the column 20 is retained by the plugs in the bubbles 23 and 24. The protective layer 25 is removed in an area 26 where light from a light source 27 passes through the column and impinges on a detector 28. The sample detection thus takes place in the zone where the bubble 24 for retaining the chromatographic packing 2 is located. This embodiment has the advantage that the pathlength for the light passing through the column is increased without requiring an additional bubble as in FIG. 2.

According to the invention it is thus possible to generate the zone serving to retain the chromatographic bed ("fritted zone") in such a way that it becomes physically impossible for the zone to be pressed out of the capillary even when it looses adhesion to the capillary wall. In an embodiment of the invention, the capillary diameter is expanded radially by a technique described in U.S. Pat. No. 5,061,361. In this way a bubble is formed in the capillary. This specific spot on the capillary will become the zone where the retaining frit is located. As one needs an inlet frit and an outlet frit, capillaries are prepared with two such bubbles at a specified distance away from each other. Packing material will not be present before and after the fritted zones so that the column length is determined by the distance between the zones and typically ranges between 5–75 cm.

By the treatment mentioned in the previous section, the particles are 'glued together' and form a porous bead with a larger diameter than the interior diameter of the preceding/following fused silica tube. Therefore the porous plug cannot move from its position. In a typical example, the heat for forming the bubble is applied by a nickel/chromium heating filament, 0.5–1.0 mm diameter which has two windings of coil diameter 2 mm. The fused silica capillary is aligned to pass through the middle of this coil. About 8 W electrical energy is applied to this coil (2 V, 4 A) from a DC power supply like the Hewlett-Packard model No. HP 6267B.

In the preferred embodiment, the fused silica capillary with bubbles containing the fritted zone can be premanufactured on the same glassblowing laithe as is used to make detection bubbles as described in U.S. Pat. No. 5,061,361. Therefore it is quite well possible to prepare a detection bubble with a higher ratio of bubble diameter to interior column diameter ("bubble factor"), of 3 to 5, in this capillary by the same process in one operation. In fact it is to great advantage for the fidelity of (electrochromatography) if such a bubble is placed within 1 cm of the outlet frit zone. The integrity of separation is maintained while simultaneously signal enhancement in the detection bubble increases sensitivity. In addition, the close vicinity of the fritted zone to the detection bubble allows it to be enclosed in the alignment device typically necessary to place the detection zone into the lightpath precisely in capillary detectors, thereby protecting the fritted zone for mechanical damage and bending stress.

Alternatively, while in the process of manufacturing of the future frit, the protective outside coating is burned off, this zone is clean and transparent for UV-Visible light and will allow spectrophotometric or fluorescence type of detection with the mentioned chromatographic signal enhancement.

In this invention fused silica tubing is used as container for the packed bed because it provides narrower columns than are typically used in high performance liquid chromatography and packed column SFC (1-5(10) mm i.d.). Fused silica has several advantages as a container for a packed bed as explained in the opening section. Therefore its usage for micro high performance liquid chromatography has gained at lot of interest lately (sev. authors). The company LC-Packings in Amsterdam, the Netherlands has an offering of fused silica capillary tubing based micro high performance liquid chromatography columns. It is understood that, even though fused silica is the preferred material for columns of the invention, other materials from which capillaries can be produced, can also be used.

As an alternative to the above described embodiment wherein an enlarged area in the interior of the column filled with material is used to retain the column bed, it is also possible to provide a constriction of the inner bore of the column for retaining the column bed. Such a constriction can be produced, for example, by appropriate drawing of the capillary when heated.

We claim:

1. A column for capillary chromatographic separations in high performance liquid chromatography, capillary electrochromatography, or supercritical chromatography, comprising:

a column bed of extended length, including packing material arranged in an inner bore of the column, and means for retaining the column bed in said inner bore of the column, said means for retaining the column bed comprising a region arranged at at least one end of the column bed and in said inner bore, which region is short relative to said extended length and is enlarged relative to said inner bore in a radial direction and which is filled with packing material, said means for retaining the column bed having a larger diameter than the inner bore preceding or following it, thereby ennhancing the ability of the means for retaining the column bed to stay in place and retain the sacking material.

2. A column as recited in of claim 1, wherein the column bed consists of silica based particles with a coating suited for high pressure liquid chromatography or electrodriven liquid chromatography.

3. A column as recited in claim 1, wherein the column bed consists of quartz or polymer based particles with a coating suited for high pressure liquid chromatography or electro-driven liquid chromatography.

4. A column as recited in claim 1, further comprising:

a detection zone, in a form of a cell positioned inside the column at an outlet side.

5. A Column as recited in claim 4, wherein the cell is arranged about 0–5 cm downstream of the means for retaining the column bed, and wherein the cell has a diameter which is about 1.5 to 5 times the diameter of the inner bore of the column.

6. A column as recited in claim 1 further comprising:

detector arrangement means for detection of sample substances separated in the column, said detector arrangement means positioned to perform said detection at a column outlet side of the means for retaining the column bed.

7. A column as recited claim 1 an inner bore of the column has a diameter between approximately 5 and 530 $\mu$m, and wherein a length of the column is between about 5 and 200 cm.

8. A column as recited in claim 1 which is made of fused silica.

9. A column as recited in claim 8 which is cut so that the means for retaining the column bed acts as a micro capillary column filter or as a pre-column.

* * * * *